US012767644B2

(12) United States Patent
Ortega Agüera et al.

(10) Patent No.: US 12,767,644 B2
(45) Date of Patent: Oct. 20, 2026

(54) USE OF 3-ARYLPHTHALIDES AND DERIVATIVES THEREOF AS ANTI-INFLAMMATORY AGENTS

(71) Applicants: UNIVERSIDAD DE CÁDIZ, Cádiz (ES); SERVICIO ANDALUZ DE SALUD, Seville (ES)

(72) Inventors: María Jesús Ortega Agüera, Puerto Real (ES); Eva Zubía Mendoza, Puerto Real (ES); Manuel Aguilar Diosdado, Cádiz (ES); Belén Parra Torrejón, Puerto Real (ES); Ana Isabel Arroba Espinosa, Cádiz (ES); María Laura Gómez Jaramillo, Cádiz (ES)

(73) Assignees: UNIVERSIDAD DE CADIZ, Cádiz (ES); SERVICIO ANDALUZ DE SALUD, Seville (ES)

( * ) Notice: Subject to any disclaimer, the term of this patent is extended or adjusted under 35 U.S.C. 154(b) by 277 days.

(21) Appl. No.: 18/292,801

(22) PCT Filed: Jun. 27, 2022

(86) PCT No.: PCT/ES2022/070405

§ 371 (c)(1),
(2) Date: Jan. 26, 2024

(87) PCT Pub. No.: WO2023/007042

PCT Pub. Date: Feb. 2, 2023

(65) Prior Publication Data

US 2025/0011295 A1 Jan. 9, 2025

(30) Foreign Application Priority Data

Jul. 29, 2021 (ES) ................................ ES202130739

(51) Int. Cl.
*C07D 307/87* (2006.01)
*A61K 31/365* (2006.01)

(52) U.S. Cl.
CPC .......... *C07D 307/87* (2013.01); *A61K 31/365* (2013.01)

(58) Field of Classification Search
CPC .................................................... C07D 307/87
See application file for complete search history.

(56) References Cited

U.S. PATENT DOCUMENTS

| | | | |
|---|---|---|---|
| 2007/0082947 A1 | 4/2007 | D'Orazio et al. | |
| 2009/0163545 A1* | 6/2009 | Goldfarb ................ | A61K 31/13 514/688 |

FOREIGN PATENT DOCUMENTS

| | | | |
|---|---|---|---|
| ES | 2327639 T3 | 11/2009 | |
| WO | WO 2008020607 A1 | 2/2008 | |
| WO | WO-2017098467 A1 * | 6/2017 | ........... A61K 31/325 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Ortega, Pharmaceuticals (2022), 15(5), 588.*
Chen et al., "Novel phthalide derivatives: Synthesis and anti-inflammatory activity in vitro and in vivo," *European Journal of Medicinal Chemistry* 206(112722), 2020 [Published online Aug. 14, 2020]. (15 pages).
Lei et al., "New Metabolites and Bioactive Chlorinated Benzophenone Derivatives Produced by a Marine-Derived Fungus *Pestalotiopsis heterocornis," Mar. Drugs* 15(69), Mar. 13, 2017. (10 pages).
Ortega et al., "Synthesis and Antioxidant/Anti-Inflammatory Activity of 3-Arylphthalides," *Pharmaceuticals* 15(588), May 10, 2022. (15 pages).
Puder et al., "New Biologically Active Rubiginones from *Streptomyces* sp.," *The Journal of Antibiotics* 53(4):329-336, Apr. 2000. (8 pages).
Strobel et al., "Isopestacin, an isobenzofuranone from Pestalotiopsis microspora, possessing antifungal and antioxidant activities," *Phytochemistry* 60(2):179-183, May 2002. (5 pages).
Teixeira et al., "Synthesis and Antiproliferative Activity of C-3 Functionalized Isobenzofuran-1(3H)-ones," *Molecules* 18:1881-1896, Feb. 1, 2013. (16 pages).
Zou et al., "Neuroprotective Effect of Phthalide Derivative CD21 against Ischemic Brain Injury:Involvement of MSR1 Mediated DAMP peroxiredoxin1 Clearance and TLR4 Signaling Inhibition," Journal of Neuroimmune Pharmacology 16:306-317, Apr. 14, 2020. (12 pages).

* cited by examiner

*Primary Examiner* — Nizal S Chandrakumar
(74) *Attorney, Agent, or Firm* — Seed Intellectual Property Law Group LLP

(57) ABSTRACT

The present invention relates to the use of 3-arylphthalides and derivatives thereof as anti-inflammatory agents. The invention relates to the use of 3-arylphthalides, in particular 3-(4,5-dihydroxy-2-(2-5 ethylthio)ethylphenyl)phthalide and 3-(2,4-dihydroxyphenyl)phthalide, as anti-inflammatory and chemopreventive agents in inflammatory processes in general, in diseases caused by underlying inflammation processes and in inflammatory processes related to the development of diabetes mellitus and its complications.

4 Claims, 1 Drawing Sheet

II

III

USE OF 3-ARYLPHTHALIDES AND DERIVATIVES THEREOF AS ANTI-INFLAMMATORY AGENTS

FIELD OF THE ART

The present invention relates to the use of 3-arylphthalides and derivatives thereof as anti-inflammatory and chemopreventive agents in inflammatory processes in general, in diseases caused by underlying inflammation processes, and in inflammatory processes related to the development of diabetes mellitus and its complications. Therefore, the present invention may be comprised in the pharmaceutical sector.

BACKGROUND OF THE INVENTION 3-arylphthalides are a class of organic molecules characterized by having an isobenzofuran-1(3H)-one base system, also referred to as phthalide, C-3 substituted with a ring or aromatic ring system. Most of the known 3-arylphthalides have been obtained by means of chemical synthesis. Several molecules of this type have also been isolated from fungi and bacteria [(Teixeira, R. R.; Bressan, G. C.; Pereira W. L.; Ferreira, J. G.; de Oliveira, F. M.; Thomaz, D. C. Synthesis and antiproliferative activity of C-3 functionalized isobenzofuran-1(3H)-ones. Molecules 2012, 18, 1881-1896), (Strobel, G.; Ford, E.; Worapong, J.; Harper, J. K.; Arif, A. M.; Grant, D. M.; Fung, P. C. W.; Chau, R. M. W. Isopestacin, an isobenzofuranone from *Pestaiotiopsis microspora* possessing antifungal and antioxidant activities. Phytochemistry 2002, 60, 179-183), (Puder, C.; Zeeck, A.; Beil, W. New biologically active rubiginones from *Streptomyces* sp. J. Antibiot. 2000, 53, 329-336), (Lei, H.; Lin, X.; Han, L.; Ma, J.; Ma, Q.; Zhong, J.; Liu, Y.; Sun, T.; Wang, J.; Huang, X. New metabolites and bioactive chlorinated benzophenone derivatives produced by a marine-derived fungus *Pestaiotiopsis heterocornis*. Mar Drugs 2017, 15, 69, doi: 10.3390/md15030069)].

Various 3-arylphthalide synthesis methods which involve constructing the C-3 substituted γ-lactone ring on an aromatic ring have been described, using as starting products (a) a benzoic acid and an aromatic aldehyde, (b) two aromatic aldehydes, (c) an N-substituted benzimidate and an aromatic aldehyde, (d) a 2-formylbenzoic acid and a phenol derivative, (e) an o-iodobenzoyl chloride and an aromatic aldehyde, (f) a 2-formylbenzoate and an arylzinc reagent, (g) a 2-formylarylcetone, or (h) a 2-acylarylcarboxylate. In relation to the C-3 chiral center of 3-arylphthalides, some of the aforementioned synthesis methods lead to obtaining racemic 3-arylphthalides, whereas various levels of enantioselectivity are reached in other methods by means of using different chiral catalysts.

From the biological activity viewpoint, only cytotoxic activity has been described for several synthetic 3-arylphthalides (Teixeira, R. R.; Bressan, G. C.; Pereira W. L.; Ferreira, J. G.; de Oliveira, F. M.; Thomaz, D. C. Synthesis and antiproliferative activity of C-3 functionalized isobenzofuran-1(3H)-ones. Molecules 2012, 18, 1881-1896). Antimycotic, antioxidant, bactericidal, and cytotoxic activities have been described for natural 3-arylphthalides [(Strobel, G.; Ford, E.; Worapong, J.; Harper, J. K.; Arif, A. M.; Grant, D. M.; Fung, P. C. W.; Chau, R. M. W. Isopestacin, an isobenzofuranone from *Pestalotiopsis microspora* possessing antifungal and antioxidant activities. Phytochemistry 2002, 60, 179-183), (Puder, C.; Zeeck, A.; Beil, W. New biologically active rubiginones from *Streptomyces* sp. J. Antibiot. 2000, 53, 329-336), (Lei, H.; Lin, X.; Han, L; Ma, J.; Ma, Q.; Zhong, J.; Liu, Y.; Sun, T.; Wang, J.; Huang, X. New metabolites and bioactive chlorinated benzophenone derivatives produced by a marine-derived fungus *Pestalotiopsis heterocornis*. Mar Drugs 2017, 15, 69, doi:10.3390/md15030069)]. All these compounds have in common the presence of the phthalide (isobenzofuran-1(3H)-one) system substituted in position 3 with an aryl group. This aryl group can consist of a single aromatic ring or an aromatic ring system, where it can further contain different substituent 3-arylphthalides attached to the carbons of the aromatic ring of the aryl group attached to position 3 of the phthalide, or to the carbons of the aromatic ring of the phthalide system.

It should be noted that there is no data concerning the anti-inflammatory activity of 3-arylphthalides.

DESCRIPTION OF THE INVENTION

The authors of the present application have found that various compounds of the class of 3-arylphthalides exhibit in vitro activity as anti-inflammatory agents.

Therefore, the present invention relates to the use of 3-(4,5-dihydroxy-2-(2-ethylthio)ethylphenyl)phthalide, 3-(2,4-dihydroxyphenyl)phthalide, and analogous compounds thereof in the preparation of pharmaceutical compositions for use in the treatment and/or prevention of inflammatory processes in general, diseases having underlying inflammation processes, and inflammatory processes related to diabetes mellitus and its complications.

Therefore, the present invention relates to the use of a compound of general formula (I) (hereinafter compound of the invention):

(I)

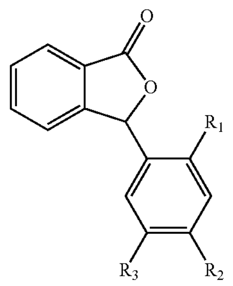

wherein: $R_1$ to $R_3$ are selected from the list comprising hydrogen, fluorine, chlorine, bromine, iodine, a ($C_1$-$C_4$) alkyl group, hydroxyl, or sulfide (R—S—R', R═$C_2$-$C_4$, R'═$C_1$-$C_4$), or of any of the pharmaceutically acceptable derivatives or stereoisomers thereof, for the manufacture of a pharmaceutical composition for the treatment and/or prevention of inflammatory processes in general, diseases caused by underlying inflammatory processes, and inflammatory processes related to diabetes mellitus and its complications.

The introduction of different substituents such as halogens (F, I, Cl, Br), alkyl chains, and other functional groups such as hydroxyl groups, or sulfide in the aromatic rings will allow improving pharmacokinetic properties such as absorption, distribution, metabolism, and excretion, [5] thereby achieving greater bioavailability of the pharmaceutical composition.

The compounds of the present invention, represented by formula (I) described above, can include any of their stereoisomers, particularly any of enantiomers (R or S) in C-3 or a racemic mixture.

The term "pharmaceutically acceptable derivatives" refers to any compound which, when administered to a recipient, is capable of providing (directly or indirectly) a compound described herein. However, it should be noted that pharmaceutically non-acceptable derivatives are also within the scope of the invention since these derivatives may be useful in the preparation of pharmaceutically acceptable derivatives. The preparation of derivatives and stereoisomers can be carried out by means of methods known in the art.

The term "alkyl" herein refers to saturated, linear, or branched hydrocarbon chains having 1 to 4 carbon atoms (methyl, ethyl, n-propyl, i-propyl, n-butyl, tert-butyl, sec-butyl, or isobutyl).

In a preferred embodiment of the present invention, $R_1$ is a 2-(ethylthio)ethyl group and $R_2$ and $R_3$ are hydroxyls, as shown in formula (II). It should be noted that this compound has not been described previously, so its structure is completely novel.

(II)

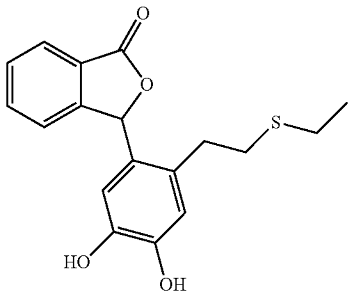

In a more preferred embodiment of the present invention, $R_1$ and $R_2$ are hydroxyls and $R_3$ is hydrogen, as shown in formula (III):

(III)

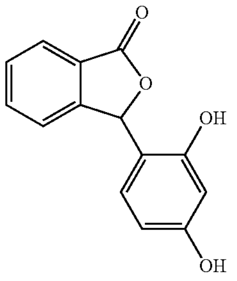

The compounds of the invention, as demonstrated in the example, can be used as anti-inflammatory agents for the following processes:

a) Diseases occurring with an underlying inflammatory process. This refers to the group of diseases that present main symptomatology and therapeutic proposal which is not aimed specifically at the mentioned inflammatory process. Pathologies of this type includes autoimmune diseases, as well as metabolic and neurodegenerative impairments.

These inflammatory processes are characterized as low-grade, chronic, underlying processes in different morbid processes that lead to considerable deterioration in the quality of life of patients suffering same.

b) Inflammatory process associated with diabetes mellitus, understood as that which occurs in early periods of the onset of the disease and participates both in triggering diabetes mellitus and in its complications. With respect to the development of diabetes mellitus itself, the presence of an inflammatory process in the pancreatic islet (where insulin-producing beta cells are housed) that directly participates in the destruction and/or reduction of the existing beta cell mass, is highlighted. Regarding its participation in complications, the inflammatory process plays an extremely relevant role in the onset and progression of both diabetic retinopathy and diabetic nephropathy.

The compound of the invention is formulated to facilitate its application and bioavailability, preferably with pharmaceutically acceptable carriers or excipients.

The compound of the invention can be used with other active ingredients or drugs which enhance anti-inflammatory effects or offer other additional benefits. Other drugs can be part of the same composition or can be provided in a separate composition for administration at the same time or at different times.

The compound of the invention can be formulated alone or with other ingredients, in the form of powders, pellets, pills, suspensions, solutions, or emulsions which may contain other compounds commonly used in the field for the preparation of products of this type.

The dosage of the compound of the invention will vary according to the particular formulation, the specific inflammatory condition to be treated, and the mode of application.

Throughout the present description, the term "treatment" refers to eliminating, reducing, or decreasing the cause or effects of the disease. For the purposes of this invention, treatment includes, but is not limited to, alleviating, reducing, or eliminating one or more symptoms of the disease; reducing the degree of disease, stabilizing (i.e., not worsening) the state of the disease, delaying or slowing down its progression, alleviating or improving the condition of the patient, and achieving partial or complete remission of the disease.

Throughout the description and claims, the word "comprises" and variants thereof do not intend to exclude other technical features, additives, components, or steps. For those skilled in the art, other objects, advantages, and features of the invention will become apparent in part from the description and in part from the practice of the invention. The following example is provided by way of illustration and does not seek to limit the present invention.

BRIEF DESCRIPTION OF THE FIGURES

The figures illustrate the synthesis and characterization of the compound of formula II, referred to as 3-(4,5-dihydroxy-2-(2-ethylthio)ethylphenyl)phthalide and the compound of formula III, referred to as 3-(2,4-dihydroxyphenyl)phthalide.

PREFERRED EMBODIMENT OF THE INVENTION

Synthesis of Compounds II and III

This example illustrates the synthesis and characterization of the compound of formula II, referred to as 3-(4,5-dihydroxy-2-(2-ethylthio)ethylphenyl)phthalide, and the compound of formula III, referred to as 3-(2,4-dihydroxy-phenyl)phthalide, and their anti-inflammatory activities.

Materials and Methods

Column chromatography was performed with Merck silica gel (70-230 μm). HPLC separations were performed in LaChrom-Hitachi equipment with LiChrospher Si-60 columns (Merck) and an L-7400 UV detector. The solvents used were of HPLC quality. NMR spectra were recorded in an Agilent 400 spectrometer using $CDCl_3$, $CD_3OD$, and $CD_3COCD_3$ as solvents. Chemical shifts were referenced with respect to the signal of the solvent ($\delta_H$ 7.26 and $\delta_C$ 77.0 for $CDCl_3$, $\delta_H$ 3.30 and $\delta_C$ 49.0 for $CD_3OD$, and $\delta_H$ 2.04 and $\delta_C$ 29.8 and 202.0 for $CD_3COCD^3$). COSY, HSQC, HMBC, and NOESY spectra were carried out using Agilent standard pulse sequences.

Synthesis

The synthesis of compounds of formula II and III is established through an electrophilic aromatic substitution of a phthalide derivative suitably functionalized with aromatic compounds 4-(2-(ethylthio)ethyl)benzene-1,2-diol and resorcinol (benzene-1,3-diol), respectively.

Figure 1:
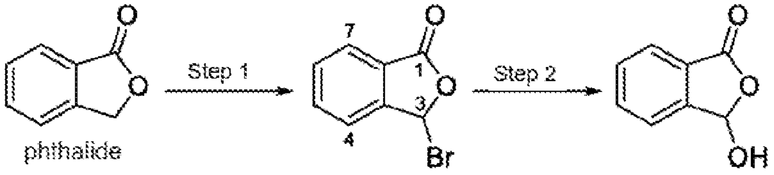
FIG. 1 illustrates radical bromination of phthalide (step 1) and obtaining 3-hydroxyphthalide (step 2).

The synthesis method starts with the commercial compound phthalide as the starting product. Phthalide has a benzylic position (C-3) that can be functionalized by means of a radical bromination process which leads to obtaining phthalide 3-bromoderivative. Suitable treatment of this bromoderivative in an alkaline medium leads to obtaining 3-hydroxyphthalide which, in acidic conditions, produces a phthalidyl ion that acts as an electrophile in an electrophilic aromatic substitution reaction with the corresponding aromatic 4-(2-(ethylthio)ethyl)benzene-1,2-diol derivatives or resorcinol. Under these conditions, compounds II and III are obtained with a good yield and purified by means of silica gel column chromatography and HPLC. This method can be described with high-performance selective transformations as shown in the following schemes of synthesis:

A) Obtaining 3-Hydroxyphthalide (FIG. 1)

Step 1: Radical Bromination of Phthalide

Phthalide (1.02 g, 7.57 mmol), NBS (1.52 g, 8.56 mmol), and benzoyl peroxide as a catalyst (51 mg, 0.19 mmol) are introduced in a 50 mL flask dissolved in 25 mL of $CCL_4$. The reaction is left under reflux for 4 h and after this time the reaction is filtered and the solvent is evaporated at reduced pressure. The residue is then dissolved in 20 mL of water and extracted with $CH_2Cl_2$ (3×20 mL). The organic phases are combined, dried on anhydrous $MgSO_4$, and the solvent is evaporated at reduced pressure, obtaining 1.60 g of 3-bromophthalide (7.52 mmol, quantitative).

3-bromophthalide characterization: $^1$H-NMR ($CDCl_3$, 399.945 MHz): δ 7.94 (1H, bd, 7.5 Hz, H-7), δ 7.78 (1H, ddd, 7.3, 7.0, 1.1 Hz, H-6), δ 7.64 (1H, bd, 7.5 Hz, H-4), δ 7.62 (1H, bd, 8.1 Hz, H-5), δ 7.40 (1H, s, H-3). $^{13}$C-NMR ($CDCl_3$, 100.576 MHz): δ 167.3 (s, C-1), δ 148.8 (s, C-3a), δ 135.2 (d, C-5), δ 130.9 (d, $C_{0-6}$), δ 125.9 (d, C-7), δ 124.1 (s, C-7a), δ 123.5 (d, C-4), δ 74.6 (d, C-3).

Step 2: Obtaining 3-hydroxyphthalide

A solution of 3-bromophthalide (500 mg, 2.35 mmol) in 25 mL of distilled $H_2O$ is treated with 200 mg of 85% KOH (3.5 mmol) and the mixture is heated under reflux for two hours. After this time, the reaction is left to reach room temperature and treated with $KHSO_4$ (170 mg). The obtained solution is extracted with AcOEt (3×25 mL). The combined organic phases are dried on anhydrous $MgSO_4$ and the solvent is evaporated at reduced pressure obtaining 409 mg of a yellow oil. This oil is purified by means of a silica gel chromatographic column (1.5×17 cm, hexane/AcOEt (6:4)), obtaining 304 mg of 3-hydroxyphthalide (2.02 mmol, Y=86%).

3-hydroxyphthalide characterization: $^1$H-NMR ($CD_3COCD_3$, 399.945 MHz): δ 7.84 (1H, bd, 8.0 Hz, H-7), δ 7.80 (1H, ddd, 7.5, 7.4, 1.0 Hz, H-5), δ 7.72 (1H, bd, 7.7 Hz, H-4), δ 7.66 (1H, bdd, 7.4, 7.4 Hz, H-6), δ 6.75 (1H, s, H-3). $^{13}$C-NMR ($CD_3COCD_3$, 100.576 MHz): δ 169.1 (s, C-1), δ 147.9 (s, C-3a), δ 135.0 (d, C-5), δ 131.3 (d, C-6), δ 127.7 (s, C-7a), δ 125.3 (d, C-1), δ 124.3 (d, C-4), d 98.7 (d, C-3).

Figure 2:
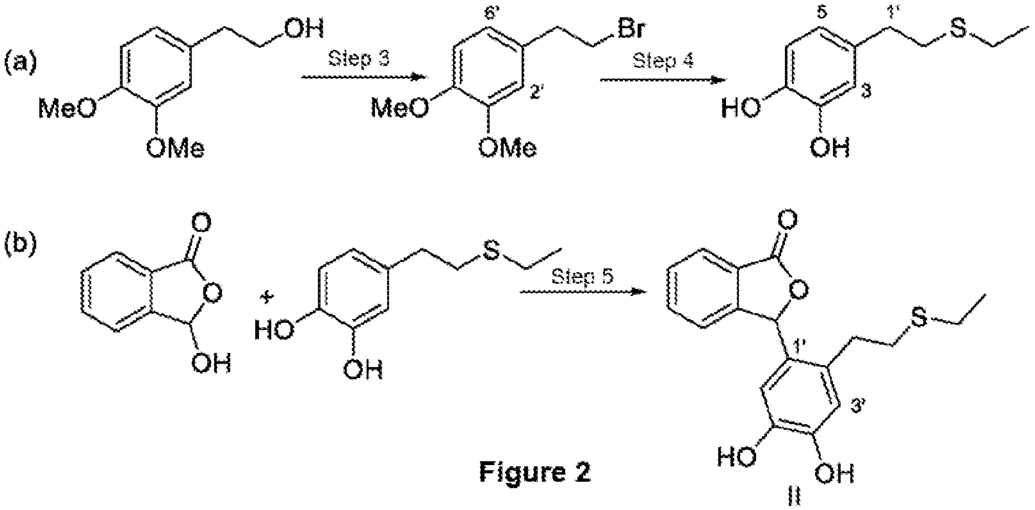
FIG. 2 illustrates bromination of 2-(3,4-dimethoxyphenyl)ethanol (step 3), obtaining 4-(2-(ethylthio)ethyl)benzene-1,2-diol (step 4), and the reaction of 4-(2-(ethylthio)ethyl)benzene-1,2-diol with 3-hydroxyphthalide (step 5) for obtaining compound II.

B) Obtaining Compound II (FIG. 2)

Step 3: Bromination of 2-(3,4-dimethoxyphenyl)ethanol 2-(3,4-dimethoxyphenyl)ethanol (0.6 g, 3.30 mmol) and $PPh_3$ (1.22 g, 4.66 mmol) dissolved in 25 mL of $CH_2Cl_2$ are introduced in a 50 mL flask cooled in an ice bath. $CBr_4$ (1.17 g, 3.52 mmol) is then added and after 5 minutes the reaction is left to react at room temperature until the starting product disappears. The reaction mixture is vacuum-concentrated and the product is purified by means of silica gel column chromatography (3×22 cm, hexane/AcOEt (7:3)), obtaining 2-(3,4-dimethoxyphenyl)ethyl bromide in a quantitative manner.

2-(3,4-dimethoxyphenyl)ethyl bromide characterization: 1H-NMR ($CDCl_3$, 399.945 MHz): δ 6.82 (1H, bd, 8.0 Hz, H-5'), δ 6.76 (1H, dd, 8.2, 1.9 Hz, H-6'), δ 6.72 (1H, bd, 1.9 Hz, H-2'), δ 3.88 (3H, s, —OMe), δ 3.86 (3H, s, —OMe), δ 3.55 (2H, t, 7.8 Hz, H-1), δ 3.10 (2H, t, 7.4 Hz, H-2). $^{13}$C-NMR ($CDCl_3$, 100.576 MHz): δ 148.9 (s, C-3'), δ 148.0 (s, C-4'), δ 131.5 (s, C-1'), δ 120.6 (d, C-6'), δ 111.9 (d, C-2'), δ 111.3 (d, C-5'), δ 39.1 (t, C-2), δ 33.2 (t, C-1).

Step 4: Obtaining 4-(2-(ethylthio)ethyl)benzene-1,2-diol

NaEtS (342 mg, 4.07 mmol) is added under inert atmosphere to a solution of 2-(3,4-dimethoxyphenyl)ethyl bromide (98 mg, 0.40 mmol) in 2 mL of dimethylformamide. The reaction mixture is brought to reflux for 3 h and after this time the solution is cooled to 0° C., treated with a 5% HCl solution, and extracted with AcOEt (3×5 mL). The combined organic phases are dried on anhydrous $MgSO_4$ and evaporation is performed under reduced pressure, leading to a residue which is purified by means of silica gel column chromatography (1.5×17 cm, hexane/AcOEt (8:2)), obtaining 63 mg of the product 4-(2-(ethylthio)ethyl)benzene-1,2-diol (0.32 mmol, Y=80%).

4-(2-(ethylthio)ethyl)benzene-1,2-diol characterization: $^1$H-NMR ($CDCl_3$, 399.945 MHz): δ 679 (1H, d, 8.4 Hz, H-6), δ 6.73 (1H, d, 1.7 Hz, H-3), δ 6.63 (1H, dd, 80, 1.9 Hz, H-5), δ 2.76-2.72 (4H, m, H-1' and H-2'), δ 2.57 (2H, c, 7.2 Hz, —$C\underline{H}_2CH_3$), δ 1.25 (3H, t, 7.6 Hz, —$CH_2C\underline{H}_3$). $^{13}C$-NMR ($CDCl_3$, 100.576 MHz): δ 143.6 (s, C-3), δ 142.0 (s, C-4), δ 133.7 (s, C-1), δ 120.8 (d, C-6), δ 115.6 (d, C-5), δ 115.4 (d, C-2), δ 35.5 (t, C-2'), δ 33.3 (t, C-1'), δ 26.0 (t, —$\underline{C}H_2CH_3$), δ 14.7 (c, —$CH_2\underline{C}H_3$).

Step 5: Reacting 4-(2-(ethylthio)ethyl)benzene-1,2-diol with 3-hydroxyphthalide (Obtaining Compound II)

5 mL of a solution of $H_2SO_4/H_2O$ (1:1) are added to a flask with 100 mg (0.67 mmol) of 3-hydroxyphthalide and left under stirring for 10'. 4-(2-(methylthio)ethyl)benzene-1,2-diol (196 mg, 0.99 mmol) is then added and left under stirring until the reaction monitoring by means of thin layer chromatography indicates the disappearance of 3-hydroxyphthalide. The reaction is neutralized with NaOH and the solution is extracted with $CHCl_3$ (3×10 mL). The organic phases are dried on anhydrous $MgSO_4$ and the solvent is evaporated at reduced pressure. The reaction crude is purified by means of a chromatographic column (2×17 cm, hexane/AcOEt (6:4)), obtaining 130 mg of compound II (0.39 mmol, Y=60%).

3-(4,5-dihydroxy-2-(2-ethylthio)ethylphenyl)phthalide characterization: $^1H$-NMR ($CD_3OD$, 399.945 MHz): δ 7.92 (1H, d, 7.6 Hz, H-7), δ 7.75 (1H, ddd, 7.8, 7.8, 1.0 Hz, H-5), δ 7.63 (1H, dd, 7.8, 7.8z, H-6), δ 7.41 (1H, dd, 7.8, 0.8 Hz, H-4), 6.78 (1H, s, H-3), δ 6.74 (1H, s, H-3'), 6.12 (1H, s, H-6'), δ 3.00-2.84 (2H, m, Ar—$C\underline{H}_2$—$CH_2$—S), δ 2.84-2.72 (2H, m, Ar—$CH_2$—$C\underline{H}_2$—S), δ 2.54 (2H, c, 7.4 Hz, —$C\underline{H}_2CH_3$), δ 1.23 (3H, t, 7.4 Hz, —$CH_2C\underline{H}_3$). $^{13}C$-NMR ($CD_3OD$, 100.576 MHz): δ 172.8 (s, C-1), δ 151.7 (s, C-3a), δ 147.7 (s, C-4'), δ 145.2 (s, C-5'), δ 135.7 (d, C-5), δ 133.9 (s, C-1'), δ 130.5 (d, C-6), δ 127.6 (s, C-7a), δ 126.1 (d, C-7), δ 126.0 (s, C-2'), δ 124.7 (d, C-4), δ 118.4 (d, C-3'), δ 115.7 (d, C-6'), δ 82.0 (d, C-3), δ 34.6 (t, Ar—$CH_2$—$CH_2$—S), δ 33.6 (t, Ar—$CH_2$—$\underline{C}H_2$—S), δ 26.9 (t, —$\underline{C}H_2CH_3$), δ 15.2 (c, —$CH_2\underline{C}H_3$).

Figure 3:
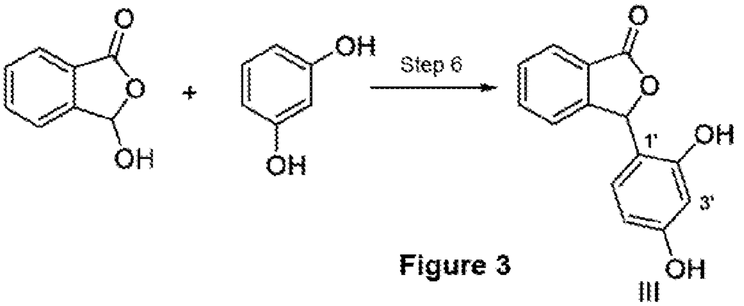
FIG. 3 illustrates the reaction of resorcinol with 3-hydroxyphthalide (step 6) for obtaining compound III.

C) Obtaining Compound III (FIG. 3)

Step 6: Reacting Resorcinol with 3-hydroxyphthalide (Obtaining Compound III)

4 mL of $H_2O$ and 1 mL of dioxane are added to a flask with 100 mg (0.67 mmol) of 3-hydroxyphthalide. 250 µl of 37% HCl are then added and left under stirring for 5 minutes. After this time, resorcinol (115 mg, 1.05 mmol) is added and left under stirring at room temperature until 3-hydroxyphthalide disappears. The reaction is neutralized with $NaHCO_3$ (500 mg) and the solution is extracted with AcOEt (3×15 mL). The organic phases are dried on anhydrous $MgSO_4$ and the solvent is evaporated at reduced pressure. The reaction crude is purified by means of a chromatographic column (2×16 cm, hexane/AcOEt (6:4)), obtaining 162 mg of 3-(2,4-dihydroxyphenyl)phthalide (0.67 mmol, Y=100%).

3-(2,4-dihydroxyphenyl)phthalide characterization: $^1H$-NMR ($CD_3COCD_3$, 399.945 MHz): δ 7.86 (1H, d, 7.8 Hz, H-7), δ 7.72 (1H, ddd, 7.4, 7.4, 1.2 Hz, H-5), δ 7.59 (1H, dd, 7.4, 7.4 Hz, H-6), δ 7.49 (1H, d, 7.8 Hz, H-4), δ 6.78 (1H, s, H-3), 6.76 (1H, d, 8.4 Hz, H-6'), 6.48 (1H, d, 2.4 Hz, H-3'), 6.31 (1H, dd, 8.4, 2.4 Hz, H-5'). $^{13}C$-NMR ($CD_3COCD_3$, 100.576 MHz): δ 171.1 (s, C-1), δ 160.2 (s, C-4'), δ 157.7 (s, C-2'), δ 151.8 (s, C-3a), δ 134.9 (d, C-5), δ 129.8 (d, C-6'), δ 128.8 (d, C-6), δ 127.2 (s, C-7a), δ 124.8 (d, C-7), δ 123.1 (d, C-4), δ 1155 (s, C-1'), δ 108.0 (d, C-5'), δ 103.8 (d, C-3'), δ 78.5 (d, C-3).

Anti-Inflammatory Activity in Immune Cell Lines Organo-specific for Type 1 Diabetes Mellitus Anti-inflammatory activity was measured on Bv.2 microglial cell line (innate immune system of the central nervous system), macrophages, Raw 264.7 cell line (peripheral immune system), renal tubular cell lines, MCT (renal tubule epithelials) and pancreatic beta cells, INS-1 (insulin-producing cells targeted in the process leading to diabetes mellitus). The cell lines were treated increasing doses of compound II or compound III for 24 h until the maximum concentration of 25 µM for compound II and 50 µM for compound III, where no cytotoxic effect was detected in any of the treated cell lines. The most potent anti-inflammatory effect was determined at the dose of 10 µM in the presence of stimulation with a bacterial lipopolysaccharide (LPS) conventionally used as an inflammation inducer in immune cell lines (Bv.2 and Raw 264.7) at a concentration of 2 $µg·mL^{-1}$, or with a proinflammatory cytokine cocktail (TNFα, IL1β, IFNγ, and TFGβ) at the concentration of 10 $ng·mL^{-1}$ in epithelial cell lines (MCTs and INS-1). The activation of the inflammatory process induces the secretion of nitrites ($NO_2$) into the medium, so the induction and modulation of the inflammatory response by 3-(4,5-dihydroxy-2-(2-ethylthio) ethylphenyl)phthalide and 3-(2,4-dihydroxyphenyl)phthalide can be determined by means of the Greiss colorimetric technique.

Tables 1 and 2 show the results of the nitrite production inhibitory activity caused by compounds II and III (10 µM), respectively, on LPS-stimulated Bv2 and Raw264.7 cell lines and on cytokine-stimulated MCT and INS-1 cell lines.

TABLE 1

Nitrite production inhibition caused by 3-(4,5-dihydroxy-2-(2-ethylthio)ethylphenyl)phthalide (compound II).

| | Baseline | LPS or cytokines | LPS or cytokines + Compound II (10 µM) | % of reduction in nitrite production |
|---|---|---|---|---|
| Bv.2 | 1.00 ± 0.01 | 3.83 ± 0.19 | 1.98 ± 0.203 | 48.31% |
| Raw 264.7 | 1.00 ± 0.02 | 6.87 ± 0.249 | 1.38 ± 0.43 | 79.88% |
| MCTs | 1.00 ± 0.01 | 8.096 ± 0.18 | 1.788 ± 0.29 | 77.91% |
| INS-1 | 1 ± 0.25 | 4.489 ± 0.03 | 3.644 ± 0.004 | 18.82% |

TABLE 2

Nitrite production inhibition caused by 3-(2,4-dihydroxyphenyl)phthalide (compound III).

| | Baseline | LPS or cytokines | LPS or cytokines + Compound III (10 µM) | % of reduction in nitrite production |
|---|---|---|---|---|
| Bv.2 | 1.00 ± 0.01 | 9.37 ± 0.92 | 3.47 ± 0.27 | 62.92% |
| Raw 264.7 | 1.00 ± 0.01 | 5.41 ± 0.39 | 3.60 ± 0.42 | 33.38% |
| MCTs | 1.00 ± 0.01 | 9.11 ± 0.71 | 1.53 ± 0.06 | 83.14% |
| INS-1 | 0.99 ± 0.04 | 4.29 ± 0.04 | 1.48 ± 0.02 | 65.32% |

In the presence of compound II (10 µM), nitrite production in LPS-stimulated Bv.2 and Raw cells decreased by 48.31% and 79.88%, respectively, and nitrite production in cytokine-stimulated MCT and INS-1 cells decreased by 77.91% and 18.82%, respectively.

In the presence of compound III (10 μM), nitrite production in LPS-stimulated Bv.2 and Raw cells decreased by 62.92% and 33.38%, respectively. In the presence of compound III (10 μM), nitrite production in cytokine-stimulated MCT and INS-1 cells decreased by 83.14% and 65.32%, respectively.

Therefore, compounds II and III exhibit a high in vitro anti-inflammatory activity in different cell types both of epithelial and immune origins.

Anti-Inflammatory Activity in Organotypic Cultures or Retinal and Kidney Explants from an Animal Model with Type 1 or Autoimmune Diabetes Mellitus Anti-inflammatory activity was determined using organotypic cultures or retinal and kidney explants from a murine model which develops type 1 or autoimmune diabetes mellitus spontaneously, i.e., BioBreeding (BB) rat. This animal model of type 1 diabetes mellitus reproduces disease progression in a manner similar to that occurring in patients. Tissues, retina, and kidney are extracted, maintaining cyto-architecture and tissue connections of each of the organs, from BB rats that are 7 weeks old, which is the time before the presence of constant hyperglycemia, which appears around weeks 9-11 of life. A prediabetic model with active inflammatory parameters that resemble those occurring during the progression of type 1 diabetes mellitus in patients is thereby obtained. The cultured explants were treated with 3-(2,4-dihydroxyphenyl)phthalide (compound III) at a dose of 20 μM for 24 h.

Activation of the inflammatory process induces nitric oxide synthase, Nos2, gene expression, with messenger RNA quantification being determined by means of the quantitative PCR technique (qPCR), and can show inflammatory response modulation in retinal and kidney explants from an animal model with type 1 or autoimmune diabetes mellitus.

Table 3 shows Nos2 expression inhibition results observed by means of treatment with 3-(2,4-dihydroxyphenyl)phthalide.

TABLE 3

Nos2 expression inhibition caused by 3-(2,4-dihydroxyphenyl)phthalide.

| | BB rat | BB rat + 3-(2,4-dihydroxy phenyl)phthalide (20 μM) | % of reduction of Nos2 expression |
|---|---|---|---|
| Retinal explant | 1.00 ± 0.01 | 0.482 ± 0.05 | 51.8% |
| Kidney explant | 1.00 ± 0.01 | 0.348 ± 0.05 | 65.2% |

The invention claimed is:

1. A compound of formula (II):

(II)

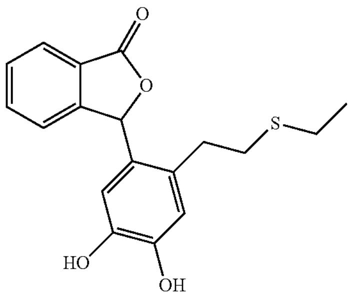

or stereoisomers thereof.

2. A pharmaceutical composition comprising the compound of claim 1, or stereoisomers thereof.

3. The pharmaceutical composition according to claim 2, comprising the compound of formula (II) as the only active ingredient.

4. The pharmaceutical composition of claim 2, further comprising another active ingredient.

* * * * *